United States Patent [19]

Engelhardt et al.

[11] 4,244,967
[45] Jan. 13, 1981

[54] ANTIPHLOGISTIC PHARMACEUTICAL COMPOSITIONS CONTAINING A PHENYLETHANOLAMINE AND METHODS OF USE

[75] Inventors: Günther Engelhardt; Johannes Keck; Gerd Krüger, all of Biberach; Klaus Noll, Warthausen; Helmut Pieper; Rainer Zimmermann, both of Biberach, all of Fed. Rep. of Germany

[73] Assignee: Boehringer Ingelheim GmbH, Ingelheim am Rhein, Fed. Rep. of Germany

[21] Appl. No.: 72,553

[22] Filed: Sep. 4, 1979

[30] Foreign Application Priority Data

Sep. 7, 1978 [DE] Fed. Rep. of Germany ....... 2838923

[51] Int. Cl.³ ............... A61K 31/17; A61K 31/27; A61K 31/275
[52] U.S. Cl. ................................. 424/300; 424/304; 424/322
[58] Field of Search ............... 424/282, 304, 330, 300, 424/322

[56] References Cited

U.S. PATENT DOCUMENTS 4,119,710  12/1979  Engelhardt ..................... 424/304

*Primary Examiner*—Stanley J. Friedman

*Attorney, Agent, or Firm*—Hammond & Littell, Weissenberger & Muserlian

[57] ABSTRACT

The method of using compounds of the formula

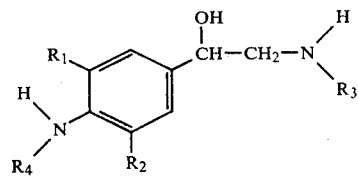

wherein
$R_1$ is hydrogen, fluorine, chlorine, bromine, iodine or cyano,
$R_2$ is fluorine, cyano, trifluoromethyl, nitro or alkyl of 1 to 4 carbon atoms,
$R_3$ is cycloalkyl or alkyl, each of 3 to 5 carbon atoms, and
$R_4$ is hydrogen or —CO—$R_5$, where
$R_5$ is alkoxy of 1 to 5 carbon atoms, alkenyloxy of 2 to 5 carbon atoms, aryloxy of 6 to 10 carbon atoms, aralkoxy of 7 to 11 carbon atoms, or amino which may be mono- or di-substituted by alkyl of 1 to 5 carbon atoms, alkenyl of 2 to 5 carbon atoms, aryl of 6 to 10 carbon atoms and/or aralkyl of 7 to 11 carbon atoms, and non-toxic, pharmacologically acceptable acid addition salts thereof as antirheumatics and antiphlogistics.

2 Claims, No Drawings

ANTIPHLOGISTIC PHARMACEUTICAL COMPOSITIONS CONTAINING A PHENYLETHANOLAMINE AND METHODS OF USE

This invention relates to antiphlogistic pharmaceutical compositions containing a phenylethanolamine as an active ingredient, and to methods of using the same as anti-inflammatories.

THE PRIOR ART

It is known that phenylethanolamines and their non-toxic acid addition salts exhibit $\beta_2$-mimetic and/or $\beta_1$-blocking properties.

For instance, U.S. Pat. No. 4,119,710 discloses phenylethanolamines of the formula

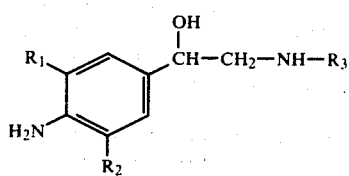

wherein
$R_1$ is hydrogen, fluorine, chlorine, bromine, iodine or cyano,
$R_2$ is fluorine, trifluoromethyl, nitro or cyano, and
$R_3$ is alkyl of 3 to 5 carbon atoms, hydroxy (alkyl of 3 to 5 carbon atoms), cycloalkyl of 3 to 5 carbon atoms, 1-(3,4-methylenedioxy-phenyl)-2-propyl or 1-(p-hydroxy-phenyl)-2-propyl,
and non-toxic, pharmacologically acceptable acid addition salts thereof, which are useful as analgesics, uterospasmolytics, bronchospasmolytics and antispastics for the skeletal musculature, and especially as $\beta_2$-receptor mimetics and $\beta_1$-receptor blockers.

Similarly, copending U.S. application Ser. No. 883,814, filed Mar. 6, 1978, discloses phenylethanolamines of the formula

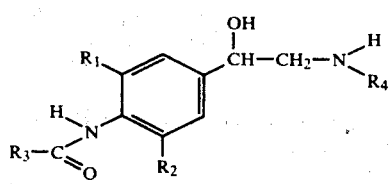

wherein
$R_1$ is hydrogen, halogen, or cyano;
$R_2$ is fluorine, cyano, trifluoromethyl, nitro or alkyl of 1 to 4 carbon atoms;
$R_3$ is alkoxy of 1 to 5 carbon atoms, alkenyloxy of 2 to 5 carbon atoms, aryloxy of 6 to 10 carbon atoms, aralkoxy of 7 to 11 carbon atoms, or —NR$_5$R$_6$, where $R_5$ and $R_6$ are each hydrogen, alkyl of 1 to 5 carbon atoms, alkenyl of 2 to 5 carbon atoms, aryl of 6 to 10 carbon atoms or aralkyl of 7 to 11 carbon atoms; and
$R_4$ is cycloalkyl of 3 to 5 carbon atoms or alkyl of 3 to 5 carbon atoms;
and non-toxic, pharmacologically acceptable acid addition salt thereof, which are useful as analgesics, uterospasmolytics and antiasthmatics.

Examples of preferred embodiments of $R_3$ in formula Ia are the following: Isopropyl, sec. butyl, isobutyl, tert. butyl, sec. pentyl, isopentyl, tert. pentyl, cyclopropyl, cyclobutyl or cyclopentyl.

Examples of preferred embodiments of $R_3$ in formula Ib are the following: Methoxy, ethoxy, n-propoxy, iso-propoxy, n-butoxy, sec. butoxy, isobutoxy, tert. butoxy, n-pentyloxy, isopentyloxy, tert. pentyloxy, phenoxy, naphthyloxy, benzyloxy, phenylethyloxy, allyloxy, butenyloxy, pentenyloxy, amino, methylamino, ethylamino, n-propylamino, isopropylamino, n-butylamino, sec. butylamino, isobutylamino, tert. butylamino, n-pentylamino, dimethylamino, diethylamino, di-n-propylamino, diisopropylamino, di-n-butylamino, di-sec. butylamino, diisobutylamino, di-tert. butylamino, di-n-pentyl-amino, phenylamino, naphthylamino, benzylamino, phenylethylamino, methylethylamino, methylbenzylamino, methyl-n-propylamino, methylisopropylamino, methyl-n-butylamino, ethyl-propylamino, ethyl-isopropylamino, diphenylamino, methylphenylamino, ethylphenylamino, isopropyl-phenylamino, allylamino, diallylamino, n-butenylamino or n-pentenylamino.

DESCRIPTION OF THE INVENTION

We have discovered that phenylethanolamines of the formula

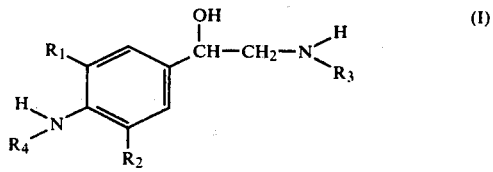

wherein
$R_1$ is hydrogen, fluorine, chlorine, bromine, iodine or cyano,
$R_2$ is fluorine, cyano, trifluoromethyl, nitro or alkyl of 1 to 4 carbon atoms,
$R_3$ is cycloalkyl or alkyl, each of 3 to 5 carbon atoms, and
$R_4$ is hydrogen or —CO—R$_5$, where
$R_5$ is alkoxy of 1 to 5 carbon atoms, alkenyloxy of 2 to 5 carbon atoms, aryloxy of 6 to 10 carbon atoms, aralkoxy of 7 to 11 carbon atoms, or amino which may be mono- or di-substituted by alkyl of 1 to 5 carbon atoms, alkenyl of 2 to 5 carbon atoms, aryl of 6 to 10 carbon atoms and/or aralkyl of 7 to 11 carbon atoms,
and non-toxic, pharmacologically acceptable acid addition salts thereof have useful antirheumatic and antiphlogistic properties.

Some of the compounds embraced by formula I are disclosed in U.S. Pat. No. 4,119,710; they and those which are not disclosed in said patent may be prepared by the methods described in Examples 1 and 2 below.

EXAMPLE 1

1-(4-Ethoxycarbonylamino-3-chloro-5-fluoro-phenyl)-2-tert.-butylamino-ethanol hydrochloride 8.7 gm of 4'-ethoxycarbonylamino-3'-chloro-5'-fluoro-acetophenone were added in portions to a solution of 3.7 gm of selenium dioxide in 30 ml of dioxane and 1 ml of water at 60° C. while stirring. The mixture obtained was refluxed for 4 hours and, after cooling, 4.1 ml of tert. butylamine were added dropwise to the solution of 4'-ethoxycarbonylamino-3'-chloro-5'-fluorophenylglyoxal thus obtained while cooling with ice. The resulting mixture was diluted with 350 ml of ethanol and filtered. 5 gm of sodium borohydride were added in portions to the filtrate containing crude 4'-ethoxy-carbonylamino-3'-chloro-5'-fluoro-phenyl-glyoxylidene-tert.-butylamine, while stirring and cooling with ice. After allowing the mixture thus obtained to stand overnight at room temperature, the excess sodium borohydride was destroyed with acetone. The resulting mixture was admixed with water and extracted with chloroform. The chloroform extract was washed with water, dried over sodium sulfate and, after the addition of activated charcoal and rapidly heated to the boiling point filtered, and evaporated in vacuo. The solid residue consisting of 1-(4-ethoxy-carbonylamino-3-chloro-5-fluoro-phenyl)-2-tert. butylamino-ethanol was admixed with isopropanol, and the mixture obtained was acidified with ethereal hydrochloric acid to pH 4. After addition of ether, the precipitated crystals were suction-filtered off and washed with ether.

M.p.: 192°–193° C.

EXAMPLE 2

1-(4-Ethoxycarbonylamino-5-bromo-3-methyl-phenyl)-2-tert.-butylamino-ethanol 6.5 gm of bromine were added dropwise into a boiling solution of 12 gm of 4'-ethoxycarbonylamino-5'-bromo-3'-methyl-acetophenone in 200 ml of chloroform, whereupon hydrobromic acid was rapidly formed. The solution obtained, containing 4'-ethoxycarbonylamino-5', 2-dibromo-3'-methyl-acetophenone, was admixed with 14.6 gm of tert. butylamine. After refluxing for 30 minutes, the resulting solution containing 4'-ethoxycarbonylamino-5'-bromo-3'-methyl-2-tert. butylamino-acetophenone was evaporated in vacuo. The residue was dissolved in 50 ml of methanol and 20 ml of water. Reduction was effected by addition thereto of a solution of 3.8 gm of sodium borohydride in 20 ml of water with simultaneous adjustment of the pH to between 6 and 8 by addition of dilute hydrochloric acid. After reduction was complete, the methanol was distilled off in vacuo. The residue obtained was admixed with water, and the resulting solution was made alkaline by addition of liquid ammonia and extracted with chloroform. The organic phase was separated, dried and evaporated in vacuo. The evaporation residue was purified on a silicagel column (eluant: chloroform/methanol 2:1). After evaporation, the residue was dissolved in ethanol, and the solution obtained was admixed with ethereal hydrochloric acid to yield 1-(4-ethoxycarbonylamino-5-bromo-3-methyl-phenyl)-2-tert. butylamino-ethanol hydrochloride.

M.p.: 212°–214° C. (decomp.).

Analogous to Examples 1 or 2, the following compounds were prepared:

1-(4-Ethoxycarbonylamino-3-chloro-5-trifluoromethyl-phenyl)-2-tert. butylamino-ethanol
M.p.: 168°–170° C. (decomp.).

1-(4-ethoxycarbonylamino-3-bromo-5-fluoro-phenyl)-2-isopropylamino-ethanol hydrochloride
M.p.: 180°–182° C.

1-(4-ethoxycarbonylamino-3-bromo-5-fluoro-phenyl)-2-tert.-butylamino-ethanol hydrochloride
M.p.: 197°–198° C. (decomp.)

1-(4-ethoxycarbonylamino-3-fluoro-phenyl)-2-tert. butylamino-ethanol hydrochloride
M.p.: 235°–236° C.

1-(4-ethoxycarbonylamino-3-cyano-5-fluoro-phenyl)-2-tert.-butylamino-ethanol hydrochloride
M.p.: 198°–200° C. (decomp.)

1-(4-ethoxycarbonylamino-3-nitro-phenyl)-2-tert. butylamino-ethanol hydrochloride
M.p.: 189°–190° C. (decomp.)

1-(4-ethoxycarbonylamino-3-fluoro-5-iodo-phenyl)-2-cyclopropylamino-ethanol
M.p.: 127°–130° C.

1-[3-fluoro-5-iodo-4-(3-methyl-ureido)-phenyl]-2-tert.butylamino-ethanol hydrochloride
M.p.: sintering from 115° C. (amorphous substance)
Mass-spectrum ($C_{14}H_{21}N_3O_2FI$): Molpeak of the base: Found: 409. Calcul.: 409.25.

1-[3-fluoro-5-iodo-4-(3-methyl-ureido)-phenyl]-2-cyclopropylamino-ethanol hydrochloride
M.p.: 167°–170° C.

1-(3-cyano-5-fluoro-4-isobutyloxycarbonylamino-phenyl)-2-tert.-butylamino-ethanol hydrochloride (The excess sodium borohydride was destroyed with dilute hydrochloric acid)
M.p.: 189°–191° C.

1-(4-benzyloxycarbonylamino-3-fluoro-5-iodo-phenyl)-2-cyclopropylamino-ethanol (The excess sodium borohydride was destroyed with dilute hydrochloric acid)
M.p.: 135°–137° C.

1-(4-allyloxycarbonylamino-3-fluoro-5-iodo-phenyl)-2-cyclopropylamino-ethanol (The excess sodium borohydride was destroyed with dilute hydrochloric acid)
M.p.: 122°–123° C.

1-(3-fluoro-4-isobutyloxycarbonylamino-5-iodo-phenyl)-2-cyclopropylamino-ethanol (The excess sodium borohydride was destroyed with dilute hydrochloric acid)
M.p.: 126°–128° C.

1-[3-cyano-4-(3-tert.butyl-ureido)-phenyl]-2-tert.butylaminoethanol
M.p.: 105°–110° C. (decomp.)
Mass-spectrum ($C_{18}H_{28}N_4O_2$) Molpeak of the base: Found 332. Calcul: 332.45.

The 4'-(3-tert.butylureido)-2-bromo-3'-cyano-acetophenone used as starting material was prepared by reaction of 4'-phenoxycarbonylamino-2-bromo-3'-cyano-acetophenone and tert.butylamine at room temperature.

1-(4-ethoxycarbonylamino-3-cyano-phenyl)-2-isopropylaminoethanol
M.p.: 112°–15° C.

1-(4-ethoxycarbonylamino-3-cyano-phenyl)-2-tert.butylaminoethanol
M.p.: 78°–82° C.

1-(4-amino-3-chloro-5-cyano-phenyl)-2-tert. butylaminoethanol
M.p.: 131°–135° C.

1-(4-amino-3-fluoro-phenyl)-2-tert.butylamino-ethanol hydrochloride
M.p.: 196°–197° C. (decomp.)

1-(4-amino-3-chloro-5-fluoro-phenyl)-2-isopropylaminoethanol hydrochloride
M.p.: 152°–154° C. (decomp.)

1-(4-amino-3-chloro-5-fluoro-phenyl)-2-cyclopropylaminoethanol hydrochloride
M.p.: 175°–177° C. (decomp.)

1-(4-amino-3-chloro-5-fluoro-phenyl)-2-tert. butylaminoethanol hydrochloride
M.p.: 206°–208° C. (decomp.)

1-(4-amino-3-chloro-5-fluoro-phenyl)-2-tert.pentylaminoethanol hydrochloride
M.p.: 187°-188° C. (decomp.)
1-(4-amino-3-bromo-5-fluoro-phenyl)-2-isopropylaminoethanol hydrochloride
M.p.: 171°-173° C. (decomp.)
1-(4-amino-3-bromo-5-fluoro-phenyl)-2-tert.butylaminoethanol hydrochloride
M.p.: 207°-208° C. (decomp.)
1-(4-amino-3-bromo-5-fluoro-phenyl)-2-cyclobutylaminoethanol hydrochloride
M.p.: 164°-166° C. (decomp.).
1-(4-amino-3-cyano-5-fluoro-phenyl)-2-isopropylamino-ethanol hydrochloride
M.p.: 182°-184° C. (decomp.)
1-(4-amino-3-cyano-5-fluoro-phenyl)-2-tert.butylaminoethanol hydrochloride
M.p.: 242°-243° C. (decomp.)
1-(4-amino-3-cyano-phenyl)-2-cyclobutylamino-ethanol hydrobromide
M.p.: from 193° C. (decomp.)
1-(4-amino-3-cyano-phenyl)-2-tert. pentylaminoethanol
M.p.: 143° C.
1-(4-amino-3-chloro-5-cyano-phenyl)-2-sec.butylaminoethanol dihydrochloride
M.p.: 190°-191° C.
1-(4-amino-3-chloro-5-cyano-phenyl)-2-tert.pentylamino-ethanol hydrochloride
M.p.: 218°-220° C. (decomp.)
1-(4-amino-3-chloro-5-cyano-phenyl)-2-cyclopentylaminoethanol hydrochloride
M.p.: 138°-144° C.
1-(4-amino-3-bromo-5-cyano-phenyl)-2-isopropylamino-ethanol hydrochloride
M.p.: 186°-189° C.
1-(4-amino-3-bromo-5-cyano-phenyl)-2-tert.butylamino-ethanol hydrochloride
M.p. 213°-215° C.
1-(4-amino-3-bromo-5-cyano-phenyl)-2-cyclobutylamino-ethanol hydrochloride
M.p.: 215°-216° C. (decomp.)
1-(4-amino-3,5-dicyano-phenyl)-2-tert.butylamino-ethanol hydrochloride
M.p.: 251°-253° C. (decomp.)
1-(4-amino-3-trifluoromethyl-phenyl)-2-tert.butylamino-ethanol hydrochloride
M.p.: 172°-174° C. (decomp.)
1-(4-amino-3-trifluoromethyl-phenyl)-2-tert. pentylaminoethanol hydrobromide
M.p.: 174°-175° C. (decomp.)
1-(4-amino-3-chloro-5-trifluoromethyl-phenyl)-2-isopropylaminoethanol
M.p.: 104°-106° C.
1-(4-amino-3-chloro-5-trifluoromethyl-phenyl)-2-tert.butylamino-ethanol hydrochloride
M.p.: 205°-207° C. (decomp.)
1-(4-amino-3-chloro-5-trifluoromethyl-phenyl)-2-cyclobutylamino-ethanol hydrochloride
M.p.: 177°-178° C.
1-(4-amino-3-chloro-5-trifluoromethyl-phenyl)-2-tert.pentylamino-ethanol hydrochloride
M.p.: 176°-178° C. (decomp.)
1-(4-amino-3-bromo-5-trifluoromethyl-phenyl)-2-isopropylaminoethanol hydrochloride
M.p.: 177°-179° C. (decomp.)
1-(4-amino-3-chloro-5-nitro-phenyl)-2-tert.butylaminoethanol
M.p.: 148°-149° C.
1-(4-amino-3-bromo-5-nitro-phenyl)-2-tert. butylaminoethanol
M.p.: 151°-152° C.
1-(4-amino-3-fluoro-5-iodo-phenyl)-2-cyclopropylaminoethanol hydrochloride
M.p.: 199°-201° C. (decomp.)

The antirheumatic and antiphlogistic properties of the compounds embraced by formula I were ascertained by the following methods:

The compounds were tested for their inhibitory effect on the release of lyosomal enzymes ($\beta$-glucuronidase was the lysomal marker-enzyme) from human polymorphnuclear leucocytes (PMN) during the phagocytosis of zymosan particles. According to WEISSMANN, the release of lyosomal enzymes in the course of the phagocytosis of immune complexes plays a significant role for the "self perpetuation" in rheumatoid arthritis. The test was performed according to the method of WEISSMANN et al. [J. Exp. Med. 134, 149s–165s (1971)]. The buffer system and the incubation times were changed, the number of the zymosan particles and the number of PMN was standardized. From the inhibiting effects produced by the test substance in comparison with the zymosan control, an $EC_{20}$ with confidence limits according to FIELLER (Quart. J. Pharm. Pharmacol. 17, 117–123 (1944) was calculated by linear regression analysis according to LINDER [Stat. Methoden, 4th Ed., 148–162, published by Birkhäuser, Basel, Switzerland (1964)] as the end concentration of the test substance that produced a 20% inhibition of the release of lysosomal $\beta$-glucuronidase from human polymorphnuclear leucocytes in vitro during the zymosan-phagocytosis.

The following table shows the results obtained from this test for a representative species of the genus represented by formula I, namely (A) 1-(4-ethoxycarbonylamino-3-cyano-5-fluoro-phenyl)-2-tert. butylamino-ethanol hydrochloride, as well as for a chemically related prior art compound, terbutaline sulfate, i.e. the sulfate of 2-tert. butylamino-1-(3,4-dihydroxy-phenyl)-ethanol (B).

Effect on the release of lysosomal $\beta$-glucuronidase from human polymorph-nucleic leucocytes under zymosan-phagocytosis.

| Compound | $n_1$ | $n_2$ | Range of the tested end concentration in mol/l | $EC_{20}$ with confidence limits in mol/l | in ng/ml |
|---|---|---|---|---|---|
| B | 4 | 103 | $10^{-8}$–$10^{-5}$ | $2.4 \times 10^{-6}$ $(1.1$–$7.3 \times 10^{-6})$ | 658.3 $(301.7$–$2002.4)$ |
| A | 3 | 147 | $10^{-8}$–$10^{-6}$ | $1.3 \times 10^{-7}$ $(0.58$–$3.1 \times 10^{-7})$ | 46.8 $(20.8$–$111.6)$ |

$n_1$ = number of the tested concentrations
$n_2$ = number of the tested charges.

Compound A was found under in vitro conditions to be a significantly stronger inhibitor of the release of lysosomal enzymes from human polymorphnuclear leucocytes than terbutaline sulfate (about 18 times stronger).

Based on that strong effect on human leucocytes and based on the long-lasting in vivo activity compared with other $\beta$-mimetics, as well as based on the very good enteral absorption, compound A is significantly more suitable than other β-mimetics to inhibit specific inflammatory conditions in patients with rheumatic diseases.

Acute toxicity

The acute toxicity was determined in mice of both sexes with an average weight of 20 gm after i.v. administration. From the number of animals which died within 14 days at various dosage levels, the $LD_{50}$ was calculated by the method of Litchfield and Wilcoxon [J. Pharmacol. exp. Ther. 96, 99 (1949)]:

| Compound | $LD_{50}$ mg/kg i.V. |
| --- | --- |
| A | 97.5 |

Thus, the compounds of the formula I and their non-toxic, pharmacologically acceptable acid addition salts are useful for the treatment of inflammations and consequently for the treatment of rheumatoid arthritis.

For pharmaceutical purposes the compounds of the formula I or their non-toxic acid addition salts are administered to warm-blooded animals perorally, parenterally, topically or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories, creams, ointments and the like. One effective dosage is from 0.083 to 1.67 mgm/kg body weight, preferably 0.16 to 0.42 mgm/kg body weight, 2 to 4 times daily.

The following examples illustrate a few pharmaceutical dosage unit compositions comprising a compound of the formula I or a non-toxic acid addition salt thereof as an active ingredient and represent the best modes contemplated of putting the invention into practical use. The parts are parts by weight unless otherwise specified.

EXAMPLE 3

Tablets

The tablet composition is compounded from the following ingredients:

| | |
| --- | --- |
| 1-(4-Ethoxycarbonylamino-3-cyano-5-fluoro-phenyl)-2-tert. butyl-amino-ethanol hydrochloride | 0.01 parts |
| Lactose | 82.49 parts |
| Potato starch | 33.00 parts |
| Polyvinyl pyrrolidone | 4.00 parts |
| Magnesium stearate | 0.50 parts |
| | 120.00 parts |

Preparation

The active ingredient and polyvinyl pyrrolidone were dissolved in ethanol. A mixture of the lactose and potato starch was homogeneously moistened with the active ingredient solution and granulated through a screen of 1.5 mm mesh size. The granulate was dried at 50° C. and passed through a screen of 1.0 mm mesh size. The granulate thus obtained was admixed with the magnesium stearate and compressed into 120 mgm-tablets.

EXAMPLE 4

Coated pills

The pill core composition is compounded from the following ingredients:

| | |
| --- | --- |
| 1-(4-Ethoxycarbonylamino-3-cyano-5-fluoro-phenyl)-2-tert. butyl-amino-ethanol hydrochloride | 0.005 parts |
| Lactose | 82.495 parts |
| Potato starch | 33.000 parts |
| Polyvinyl pyrrolidone | 4.000 parts |
| Magnesium stearate | 0.500 parts |
| Total | 120.000 parts |

Preparation

The pill cores are prepared in analogy to Example 3 and are then coated with a thin shell consisting essentially of a mixture of talcum and sugar. The coated pills are finally polished with beeswax.

EXAMPLE 5

Gelatin capsules

The capsule filler composition is compounded from the following ingredients:

| | |
| --- | --- |
| 1-(4-Ethoxycarbonylamino-3-cyano-5-fluoro-phenyl)-2-tert. butyl-amino-ethanol hydrochloride | 0.01 parts |
| Lactose | 59.99 parts |
| Corn starch | 60.00 parts |
| Total | 120.00 parts |

Preparation

The active ingredient was intimately mixed with the lactose and corn starch, and 120 mgm-portions of the mixture were filled into gelatin capsules of suitable size.

EXAMPLE 6

Hypodermic solutions

The solution is compounded from the following ingredients:

| | |
| --- | --- |
| 1-(4-Ethoxycarbonylamino-3-cyano-5-fluoro-phenyl)-2-tert. butyl-amino-ethanol hydrochloride | 0.01 parts |
| Citric acid | 2.5 parts |
| Sodium hydrogen phosphate | 7.5 parts |
| Sodium chloride | 4.6 parts |
| Distilled water q.s. ad | 2000.0 parts by vol. |

Preparation

The active ingredient, the buffers and the sodium chloride were dissolved in the distilled water, and the solution was filtered until free from suspended matter. The filtrate was filled into 2 cc-brown ampules in an atmosphere of nitrogen, and the filled ampules were sterilized for 20 minutes at 120° C. and then sealed.

EXAMPLE 7

Suppositories

The suppository composition is compounded from the following ingredients:

| | |
|---|---|
| 1-(4-Ethoxycarbonylamino-3-cyano-5-fluoro-phenyl)-2-tert. butyl-amino-ethanol hydrochloride | 0.01 parts |
| Suppository base (e.g. cocoa butter) | 1699.99 parts |
| Total | 1700.00 parts |

Preparation

The finely pulverized active ingredient was stirred with the aid of an immersion homogenizer into the suppository base which had been melted and cooled to 40° C. 1700 mgm-portions of the composition were then poured at 37° C. into cooled suppository molds and allowed to harden therein.

EXAMPLE 8

Syrup

The syrup is compounded from the following ingredients:

| | |
|---|---|
| 1-(4-Ethoxycarbonylamino-3-cyano-5-fluoro-phenyl)-2-tert. butyl-amino-ethanol hydrochloride | 0.001 parts |
| Benzoic acid | 0.1 parts |
| Tartaric acid | 1.0 parts |
| Sugar | 50.0 parts |
| Flavoring | 1.0 parts |
| Food color | 0.05 parts |
| Distilled water q.s. ad | 100.0 parts by vol. |

Preparation

About 60 gm of distilled water was heated to 80° C., and the benzoic acid, the tartaric acid, the active ingredient, the food color and the sugar were successively dissolved therein. The solution was allowed to cool to room temperature, whereupon the flavoring was added and the mixture was diluted with distilled water to the indicated volume. The syrup was finally filtered. 10 ml of the finished syrup contained 10 gr of active ingredient.

Any one of the other compounds embraced by formula I or a non-toxic, pharmacologically acceptable acid addition salt thereof may be substituted for the particular active ingredient in Examples 3 through 8. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of counteracting inflammation in a warm-blooded animal in need thereof, which comprises perorally, parenterally or rectally administering to said animal an effective antiphlogistic amount of a compound of the formula

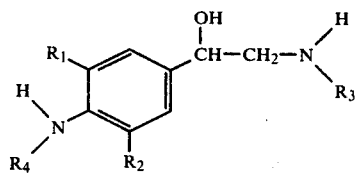

wherein
$R_1$ is hydrogen, fluorine, chlorine, bromine, iodine or cyano,
$R_2$ is fluorine, cyano, trifluoromethyl, nitro or alkyl of 1 to 4 carbon atoms,
$R_3$ is cycloalkyl or alkyl, each of 3 to 5 carbon atoms, and
$R_4$ is hydrogen or -CO-$R_5$, where
$R_5$ is alkoxy of 1 to 5 carbon atoms, alkenyloxy of 2 to 5 carbon atoms, aryloxy of 6 to 10 carbon atoms, aralkoxy of 7 to 11 carbon atoms or amino, which may be mono- or di-substituted by alkyl of 1 to 5 carbon atoms, alkenyl of 2 to 5 carbon atoms, aryl of 6 to 10 carbon atoms and/or aralkyl of 7 to 11 carbon atoms,
or a non-toxic, pharmacologically acceptable acid addition salt thereof.

2. The method of claim 1, wherein said compound is 1-(4-ethoxycarbonylamino-3-cyano-5-fluoro-phenyl)-2-tert. butylamino-ethanol hydrochloride.

* * * * *

UNITED STATES PATENT AND TRADEMARK OFFICE
CERTIFICATE OF CORRECTION

PATENT NO. : 4,244,967
DATED : January 13, 1981
INVENTOR(S) : GÜNTHER ENGELHARDT ET AL.

It is certified that error appears in the above—identified patent and that said Letters Patent is hereby corrected as shown below:

Column 4, line 50: "112°-15°C." should read
-- 112°-115°C. --

Column 6, lines 15/16: "WEIS-SMANN" should read
-- WEISS-MANN --.

Column 9, line 31: "0.001 parts" should read
-- 0.0001 parts --.

Signed and Sealed this

Twelfth Day of May 1981

[SEAL]

Attest:

RENE D. TEGTMEYER

Attesting Officer     Acting Commissioner of Patents and Trademarks